United States Patent
Kueny

(10) Patent No.: US 7,049,156 B2
(45) Date of Patent: May 23, 2006

(54) SYSTEM AND METHOD FOR IN-SITU MONITOR AND CONTROL OF FILM THICKNESS AND TRENCH DEPTH

(75) Inventor: Andrew Weeks Kueny, Dallas, TX (US)

(73) Assignee: Verity Instruments, Inc., Carrollton, TX (US)

( * ) Notice: Subject to any disclaimer, the term of this patent is extended or adjusted under 35 U.S.C. 154(b) by 454 days.

(21) Appl. No.: 10/392,991

(22) Filed: Mar. 19, 2003

(65) Prior Publication Data

US 2004/0185582 A1 Sep. 23, 2004

(51) Int. Cl.
*G01L 31/26* (2006.01)

(52) U.S. Cl. .................................................. 438/16
(58) Field of Classification Search ................ 356/357; 355/53; 250/548
See application file for complete search history.

(56) References Cited

U.S. PATENT DOCUMENTS

| | | | |
|---|---|---|---|
| 4,988,198 A | 1/1991 | Kondo | |
| 5,392,118 A | 2/1995 | Wickramasinghe | |
| 5,555,472 A * | 9/1996 | Clapis et al. | 356/504 |
| 5,587,792 A | 12/1996 | Nishizawa et al. | |
| 5,900,633 A | 5/1999 | Solomon et al. | |
| 6,281,974 B1 | 8/2001 | Scheiner et al. | |
| 6,590,636 B1 * | 7/2003 | Nishi | 355/53 |

* cited by examiner

*Primary Examiner*—Michael Lebentritt
(74) *Attorney, Agent, or Firm*—Rudolph J. Buchel, Jr.

(57) ABSTRACT

The present invention is directed to a system, method and software program product for calculating metrological data (e.g. layer thicknesses and depths of recesses and trenches) on a surface or structure, such as a semiconductor wafer. The present method does not require knowledge of the reflectivity or transmissivity of the surface or structure, but only a quantity related to the reflectivity or transmissivity linear transformation needs to be known. Initially, a simplified optical model for the process is constructed using as many parameters as necessary for calculating the surface reflectivity of the discrete regions on the wafer. Reflectivity data are collected from the surface of a wafer using, for instance, in-situ monitoring, and nominal reflectivity is determined from the ratio of the current spectrum to a reference spectrum. The reference spectrum is taken from a reference wafer consisting entirely of a material in which the reflection properties are well characterized. Both the observed and calculated data are transformed such that their vertical extents and spectrally averaged values coincide. By transforming both the observed data and calculated model such that their vertical extents and spectrally averaged values coincide, large errors in both the data and the model can be tolerated. A merit function is employed which measures the agreement between observed data and the model with a particular choice of parameters. The merit function may be minimized using a standard numerical technique for finding a deep minimum in the merit function at the correct values of the parameters.

42 Claims, 11 Drawing Sheets

SYSTEM AND METHOD FOR IN-SITU MONITOR AND CONTROL OF FILM THICKNESS AND TRENCH DEPTH

BACKGROUND OF THE INVENTION

1. Field of the Invention

The present invention relates to semiconductor processing. Still more particularly, the present invention relates to a system, method and computed program product for monitoring the film thickness and trench depth in a semiconductor process.

2. Description of Related Art

Semiconductor processing techniques used e.g., for the fabrication of integrated circuits and microelectromechanical systems (MEMS) employ multiple processing steps aimed at creating or removing a film of material in a layer, or creating or removing selectively parts of layers to create topography on these layers. Examples include plasma etching and chemical vapor deposition processes.

The final result of these processes is often required to have a precisely controlled dimension such as the thickness of a film or the depth of a trench. An example is the excavation of trenches in silicon to make transistors by the Shallow Trench Isolation (STI) process. In this case, the incoming part is a silicon wafer which has had deposited on it a stack comprising multiple layers. The top layer is a mask, typically photoresist, which has openings in the form of trenches in it. During the STI process, the pattern of openings will be transferred to the silicon by etching trenches into the silicon, wherever there is an opening in the mask. During this step the mask itself may also be etched. It is desirable to control the final depth of the trench in the silicon to within a few nanometers. Because the trench is cut through the mask and all subsequent layers into the silicon, knowing the depth of the trench into the silicon requires knowledge of both the total trench depth and the thicknesses of all intermediate layers.

This high degree of precision is typically achieved by maintaining strict control of the thicknesses of the layers on the incoming wafer, and of the etch process itself. The prior art achieves the necessary degree of control by employing a complex multi-step approach. Once the etch process is considered stable, it is run on one or more test cases. The resulting wafer is then taken to a metrology station where the relevant thicknesses and depths are measured. The metrological techniques are typically Scanning Electron Microscopy (SEM) or Atomic Force Microscopy (AFM), which are destructive, or optical measurements. These measurements provide a calibration which allows the etch rates to be inferred. Then the necessary precision of the layer thickness or trench depth can be achieved simply by controlling the time of the etch step. During production etching, additional wafers are periodically pulled from production and measured using the techniques described above to ensure that the process remains in control. If necessary, either the etch time or etch rate is then adjusted to bring the thicknesses or depths back to the target.

Although this technique works well to achieve the necessary control, it has two undesirable aspects. First is the cost, in material, time and labor, to perform the calibration measurements. Second, this mode of operation requires that the process be maintained much more precisely than would otherwise be necessary.

Periodic measurements are then required to ensure that the necessary control is being maintained. If destructive measurement techniques are used, this entails an additional cost in the form of lost product. Finally, if control is lost, by the time the necessary measurements have been performed so that this becomes known, additional out-of-spec product will have been produced.

For this reason, it would be desirable to have a technique that allows the trench depths and layer thicknesses to be measured continuously, in-situ, on each wafer, during the production etch. In-situ measuring trench depths and layer thicknesses would reduce the need for off-line metrology steps, eliminate the production of out-of-spec product, and allow larger tolerances to be used for control of the process. Making the measurement in-situ, however, is more difficult than making it at a dedicated metrology station. Methods which require contact with the wafer, or are destructive, cannot be considered, so optical methods are preferred. Optical methods in the prior art which are compatible with in-situ real time measurement exist, but generally lack the sophistication to measure quantities on patterned device wafers of current interest.

For example, a method for measuring the thicknesses of layers in a multi-layer film stack is disclosed in Nishizawa, et al. in U.S. Pat. No. 5,587,792, which is incorporated herein by reference in its entirety. Nishizawa, et al. describe an apparatus for measuring the thickness of the layers of a thin semiconductor multi-layer film by irradiating the multi-layer semiconductor film with light having a wavelength range between visible and infrared light spectrum and a photometry system for continuous spectrometry of the reflected light from the multi-layer film, such as a Michelson interferometer. The interference waveform dispersion spectrum of light reflected from the multi-layer film is compared to a waveform obtained by numerical calculation using an optical characteristic matrix. Respective layer thickness values obtained from the calculated analysis of the spatial interference waveform are subjected to waveform fitting with actually measured values. The theoretical interference spectrum is recalculated while changing approximate values of the layer thicknesses until a match is obtained to obtain precise respective layer thicknesses.

The above described film thickness measurement technique requires that a homogeneous film stack exist throughout the area being measured. The features on modem device wafers are small and densely packed, so adapting this technique to such a wafer would require the use of a very small optical probe (i.e., illumination spot), and probably also the ability to translate the beam to locate the desired area for measurement. Doing so is difficult and impractical for an in-situ measurement.

Methods for measuring the depth of a trench are described by Kondo in U.S. Pat. No. 4,988,198, and Wickramasinghe in U.S. Pat. No. 5,392,118, each of which are incorporated herein by reference in there entirety. These methods exploit interference phenomena which occur when a light beam is partially reflected from both the top and bottom of a trench. Trench depth is inferred from the spacing of adjacent minima or maxima in the reflected light signal from the wafer. The reflection may be monitored as a function of time, in which case only relative depth information is obtained. It may also be monitored as wavelength or incidence angle is varied, in which case absolute depth information may be obtained.

These methods are also inadequate for problems like the STI case described above, because they only yield the total trench depth. They are also difficult to apply when the trenches are cut into a multilayered structure.

Recently there have been efforts to overcome these limitations by using more sophisticated algorithms in conjunction with optical reflectometry. The idea is to use a broad wavelength range and measure the spectral reflectivity over an extended spot on the wafer which includes two or more discrete regions, each with a different, possibly multi-layer, film stack. Surface topography on the wafer is accommodated by recognizing that the upper surfaces of the respective regions may not all lie in a single plane.

All of the prior art methods discussed above make use of the fact that the reflectivity of structures of the sort we are concerned with is determined by multiple interference effects. A light photon which has been reflected from the structure and then detected may be considered to have taken any of a large number of alternative paths. These paths may differ in having been reflected from different regions in the plane of the wafer, if these regions are separated by a distance less than the lateral coherence length of the light. Paths which undergo different combinations of reflections at the interfaces are also present, provided that their lengths differ by no more than the longitudinal coherence length of the light. The contributions from all of these paths add, and their relative phases determine whether they add destructively or constructively, hence the intensity of the observed signal. The phases are determined by the ratio of the path length difference to the wavelength. Where the interference is primarily constructive, the reflectivity is high, and where it is primarily destructive, it is low. This is the main way in which information about layer thicknesses and trench depths is embedded in the reflection spectrum. The magnitude of the reflectivity, and the amplitude of the variation of the magnitude from one wavelength to another, are primarily determined by the size of the refractive index discontinuity at the various interfaces and the relative sizes of the different regions—things which are incidental to the vertical dimensions of the structure which we are trying to monitor, although they are important if the reflectivity is to be matched by an optical model.

The methods rely on the use of an optical reflectivity model which is sufficiently detailed to account for each different area within the measured spot. The model takes the form of a function of several parameters. Each layer thickness and each trench depth within each discrete area is represented by a parameter in the model. In general there will be other parameters as well. The measurement of unknown layer thicknesses and trench depths is achieved by varying the values of the respective parameters until the difference between the observed spectrum and the model is minimized.

A general description of the method is disclosed by Solomon et al. in U.S. Pat. No. 5,900,633, which is incorporated herein by reference in its entirety. Thickness and composition of layers fabricated during manufacture can be determined using a measurement spot that is sufficiently large to irradiate areas of two or more different regions of the sample that result from its patterned features, generally at replicable locations. One or more of reflectance, transmittance, and radiance spectrance is measured, and the various parameters characterizing the thickness and composition in the patterned areas are obtained using, for example, a model-based analysis of the polarization and amplitude of the emanating radiation, the model parameters being iteratively adjusted to achieve a match with measured values. Measurements may be taken both before and also after treatment steps are effected, and/or by using measurements from the same location on designated samples undergoing the same process, to reduce the number of unknown parameters in a reference model, thus increasing the practicality and speed of the method.

Scheiner, et al. in U.S. Pat. No. 6,281,974 B1, disclose another description of substantially the same method described immediately above and is also incorporated herein by reference in its entirety. Scheiner, et al. state that the measuring method uses at least one desired parameter of a patterned structure having a plurality of features defined by a certain process of its manufacturing. The structure being represents a grid having at least one cycle formed of at least two locally adjacent elements having different optical properties in respect of an incident radiation. The method further employs an optical model which is based on at least some of the features of the structure and is capable of determining theoretical data representative of photometric intensities of light components of different wavelengths specularly reflected from the structure. The optical model also is capable of calculating the desired parameter of the structure. Essentially, a measurement area, which is substantially larger than a surface area of the structure defined by the grid cycle, is illuminated by an incident radiation of a preset substantially wide wavelength range. Light component substantially specularly reflected from the measurement area is detected, and measured data representative of photometric intensities of each wavelength within the wavelength range is obtained. The measured and theoretical data satisfies a predetermined condition. Upon detecting that the predetermined condition is satisfied, the desired parameter of the structure is calculated.

Another disclosure of a similar method is provided by Zalicki in U.S. Pat. No. 6,275,297, which is incorporated herein by reference in its entirety. The method disclosed by Zalicki is specifically intended for STI trench depth measurement. Zalicki describes measuring a depth geometry of a structure on a semiconductor substrate that includes a plurality of recessed and non-recessed portions, wherein one of the recessed and non-recessed portions includes a reference interface and one of the recessed and non-recessed portions has a dielectric layer thereon. The apparatus for measuring uses a broadband light source for irradiating the substrate and a detector for detecting a first spectral component comprising light reflected from the non-recessed portions, a second spectral component comprising light reflected from the recessed portions, and a third spectral component comprising light reflected from the dielectric layer. Spectral reflectance information of the detected rays is stored and a plot of reflectance intensity versus wavelength is generated. A depth geometry of one of the recessed portions and the dielectric layer are determined relative to the reference interface, based on an interferometric analysis of the plot, with the ability to distinguish depth geometries with a resolution as low as 100 angstroms. Zalicki further states that the method may be performed in-situ and that the analysis for determining the depth geometries preferably includes fitting the plot to a reflectance model.

With regard to the apparatus used to make the reflectivity measurement which forms the basis of these methods, the physical apparatus may take many forms, depending upon whether the measurement is to be made in-situ or in line, which wavelengths of light are to be employed, and many other factors. Descriptions of suitable arrangements are given by K. P. Kileen and W. G. Breiland (J. Electron Mater 23, 179 (1994), and Optical Diagnostics for Thin Film Processing by I. P. Herman, Academic Press (1996), p. 358), and by Perry, et al. in U.S. Pat. No. 6,160,621, for example, each of which are incorporated herein by reference in their entireties. It is a general requirement for each of these methods that the apparatus be capable of returning accurately the reflectivity of the surface being measured for a substantially broad range of wavelengths.

In each of these implementations, this method requires the construction of an optical model which is sufficiently complete so as to afford substantial agreement with the observed reflection spectrum when the appropriate values for the parameters are used. The model takes the form of an equation which includes parameters representing the quantities to be determined.

Standard minimization techniques are used to find the values of the parameters which produce the best agreement between the calculated model and the observed reflection spectrum. Agreement in this context means the minimization of a "merit function" defining a so-called "goodness of fit" between the measured and theoretical data. None of the prior art references mentioned above explicitly teaches how this merit function is to be defined, or how the minimization is to be done. However, the standard form of the merit function is the sum of the squares of the difference between the observed and calculated spectrum at some or all of the wavelengths for which measurements exist. Solomon et al. suggest that the Levenberg-Marquardt method can be used to perform the non-linear regression analysis (Press, W. H., Flannery, B. P., Teukolsky, S. A., Vetterling, W. T., Numerical Recipes, Cambridge University Press, 1992.) It can be problematic to apply such techniques to oscillatory data of the sort generated by these optical methods, however, because the merit function typically has many local minima which correspond to incorrect values for the parameters. These techniques require an initial guess for each of the parameters being determined, and there is always the danger that the algorithm will converge to a nearby local minimum rather than the global minimum which is the correct answer.

It is of key importance to the success of these methods that the merit function have a well-defined minimum, and that this minimum actually occur for the values of the parameters which correspond to the correct values of the thicknesses and depths being determined. If not, then it becomes likely that some combinations of incorrect values will yield values of the merit function which is nearly as low as, or even lower than, that of the correct values. With the prior art methods, this imposes the requirement that the optical model be capable of accurately reproducing the observed reflectance of the structure. In order to make this so, it is generally found to be necessary to include, in addition to the parameters representing the quantities to be measured, additional parameters representing other properties of the structure.

Examples of such parameters include:
1) The optical constants n and k of each layer in each area at each wavelength used;
2) The relative areas of the different discrete areas, Solomon, et. al. (col. 9, line 41), Scheiner et al. (col. 9, line 60, describing parameters $C_1$, $C_2$ and $C_3$), and Zalicki (col. 7, line 37);
3) A parameter describing scattering from the sides of trenches, Zalicki (col. 7, line 37 describing parameter $C_4$),
4) A parameter $\lambda$ describing the coherence of the light in the optical system, Scheiner et al. (col. 7, line 35, describing parameter $\lambda$);
5) Heuristic "size coupling factors," Scheiner et al. (col. 8, line 16, describing parameters $c_1$ and $c_2$);
6) Dissipation factors, Scheiner et al. (col. 8, line 43, describing parameters b2 and B); and
7) Polarization factors, Scheiner et al. (col. 9, line 10. describing parameters $p_1$ and p2)

These prior art methods are potentially suitable for in-situ metrology because a small illuminated spot is not required. However, the prior art methods mentioned above are generally limited in their usefulness for continuous in-situ monitoring due to several factors previously unaddressed in the prior art.

One shortcoming is that the prior art methods require an accurate measurement of the reflectivity of the wafer over a broad range of wavelengths. The reflectivity is the ratio of the incident to reflected optical power from the wafer. In an in-situ measurement, neither the beam incident on nor reflected from the wafer is directly accessible to measurement. Hence, the reflectivity has to be inferred from a measurement which is a convolution of the reflectivity and some other system properties, such as the transmission of a window. If these properties are unknown, or if they are subject to change, then the inference requires the addition of further parameters.

Another problem which the prior art has failed to fully address is minimization. The minimization problem which should be solved in order to make a measurement entails a search over a parameter space whose dimension is higher than the number of unknowns being determined. At minimum, there must be one fitted parameter for each of the quantities being determined. Because these methods depend on finding an accurate fit between the observed and calculated reflectivity, however, additional parameters, such as mentioned (e.g., parameters for describing: scattering from the sides of trenches; the coherence of the light in the optical system; heuristic "size coupling factors;" dissipation factors; and polarization factors), must in general be used. Each additional fitting parameter which is required raises the level of difficulty of the problem.

Finally, the prior art reliance on the requirement of a substantially accurate fit imposes the limitation that the model be specific to a narrow range of structures for which it is suitable. This makes it inconvenient to use in a production environment where structures of many different kinds are processed, since different forms of the model have to be used with different structures.

SUMMARY OF THE INVENTION

A method for in-situ monitoring and control of film thickness and trench depth is disclosed in accordance with an exemplary embodiment of the present invention. Trench depths on a process wafer are accurately calculated in real-time using a simplified optical model which employs a reduced parameter set, and a novel merit function that is sensitive primarily to the positions of maxima and minima in the reflectivity.

The observed spectrum from a process wafer is matched to a calculated spectrum without the necessity of a substantially good fit between observed and calculated spectra. This allows for the use of the simpler optical model with a reduced set of parameters. It also allows the use of compromised reflectivity data such as might be realized in practice in an actual in-situ monitoring environment. The method further involves constructing a merit function for comparison between observed and calculated data which is preferentially sensitive towards those aspects of the observed and calculated data which are determined by the thicknesses of the layers, and yet insensitive to those aspects which are determined by other aspects of the structure not of interest.

According to one aspect of the present invention, a real-time stream of spectral reflectivity data from the surface of a production wafer is monitored in real-time and the vertical range of the observed data is rescaled to the vertical range of the calculated data, which relaxes the requirement of accurately calculating the reflectivity. Next, the data is reduced to a minimal set which facilitates fast computation but preserves the information content of the original spectrum. One exemplary method for reducing the data involves subdividing the spectrum into N small regions whose endpoints have evenly spaced reciprocals, and then average the wavelength and the reflectivity within each region to obtain a single (wavelength, reflectivity) ($\lambda$, $R^{obs}$) pair for each region, i. The number of regions chosen is large enough so that the smallest features of interest in the reflectivity spectrum span four or more regions. The spectral data used for fitting can then be thought of as a list $R^{obs}$ of length N without explicit reference to wavelength.

Having determined a value N for the process wafer, an optical model $R^c(\lambda, p_1, P_2, \ldots, p_n)$ is created and evaluated at N wavelengths, one per partitioned region. The result is a list $R^c$ of length N for comparison with the observed data $R^{obs}$ which is also in the form of a list of length N. Once the partition is decided, list $R^c$ becomes a function only of as many parameters $p_i$ as are required, and to make this explicit we may write it as $R^c(p_1, p_2, \ldots, p_n)$.

The observed data $R^{obs}$ and the model $R^c(p_1, p_2, \ldots, p_n)$ are compared using a merit function $M_1(p_1, p_2, \ldots, p_n)$. However, the vertical range of the data, whether calculated or observed, is scaled according to the maximum and minimum values contained within it. Both the observed data and the calculated model data are rescaled prior to comparing the two through the merit function. Moreover, both the observed data and calculated model are transformed such that their vertical extents and spectrally averaged values coincide. With the transformed data and an appropriately constructed merit function, a deep minimum can be found at the correct values of the parameters even with large errors in both the observed data and the calculated model. Minimization of the merit function is achieved by standard numerical techniques known in the prior art or in accordance with another aspect of the present invention, or might instead be achieved though an exhaustive search of the entire parameter space on a discrete grid. The second minimization option is possible in cases where the number of parameters being searched is small, such as where only two thickness parameters are to be used.

BRIEF DESCRIPTION OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

FIG. 4 depicts the optical model constructed in accordance with an exemplary embodiment of the present invention evaluated for the correct values of $p_1$ nm and $p_2$ nm at two different values of the parameter a;

Other features of the present invention will be apparent from the accompanying drawings and from the following detailed description.

DETAILED DESCRIPTION OF THE INVENTION

Figure 1:
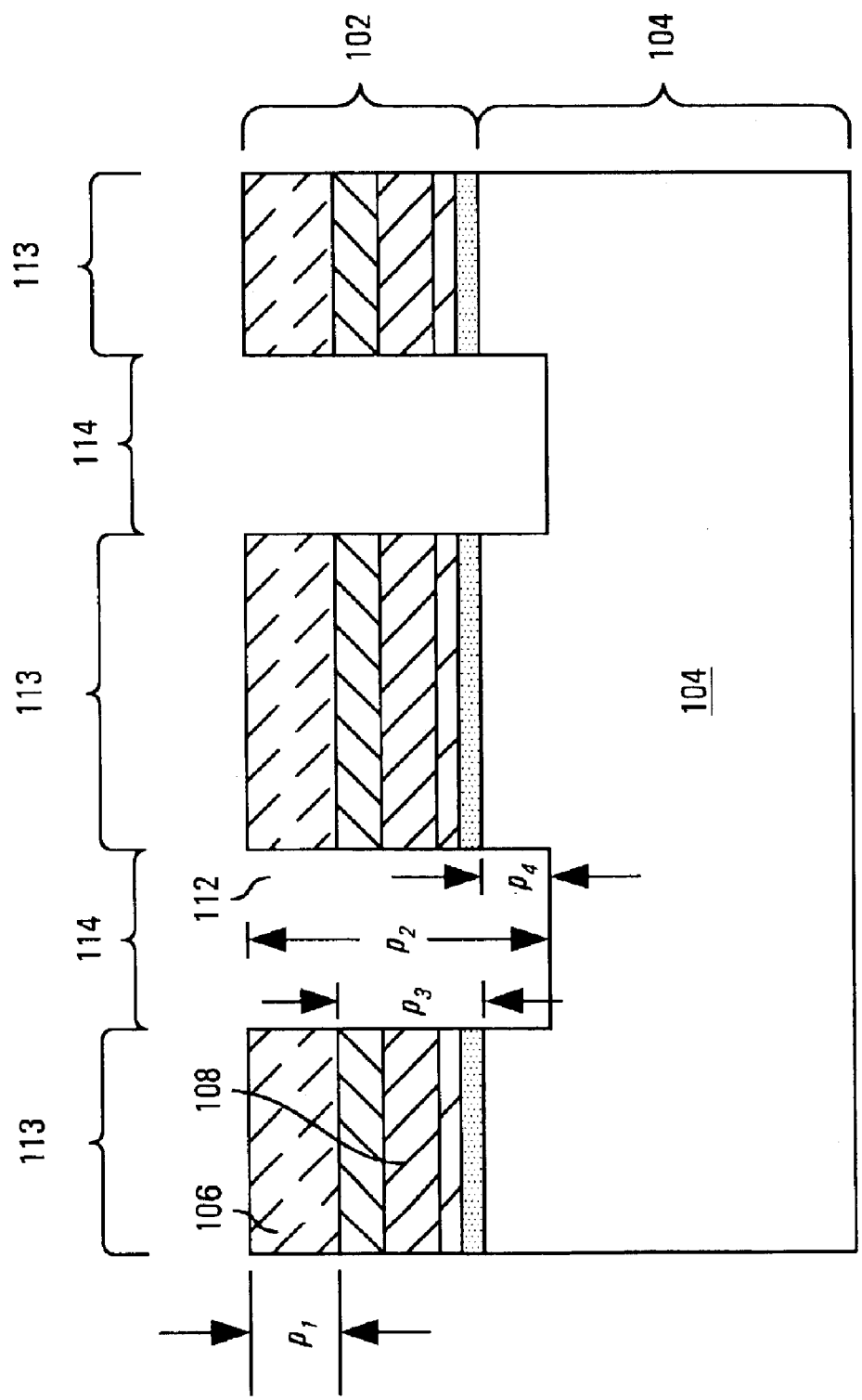
FIG. 1 is a diagram of a cross-sectional view of an exemplary STI structure.

FIG. 1 is a diagram of a cross-sectional view of an exemplary STI structure. The present STI structure is comprised of two discrete region types; region 113 and region 114. The first type, region 113, is a multilayer dielectric stack 102 on top of a silicon substrate 104. Top layer 106 of the multilayer dielectric stack forming region 102 is photoresist. Below top layer 106 are intermediate layer(s) 108. The thickness of each layer in region 113 is known except for top layer 106 which is not known i.e., the thicknesses of intermediate layer(s) 108 are known. Region 114, the second type of region, is in the exemplary STI structure comprised of substrate 104, since in the depicted exemplary STI structure, trench 112 initially extends through region 108 and to or into region 104.

Trench 112 is formed as result of a trench excavation process, the type of which is unimportant for the purpose of describing the present invention, but may be any known process such as plasma etching, or may be a currently unknown type of etching. In the depicted example, trench 112 traverses region 102 and extends into region 104; however, it should be understood that the process depicted is merely exemplary, and the method could also be applied to a case where region 114 has a more complex structure. With further reference to the depicted example, the thickness of top layer 106 is shown as film thickness $p_1$ and the total depth of trench 112 is identified as trench depth $p_2$. The thickness of intermediate layer(s) 108 is represented as known thickness $p_3$. The portion of trench 112 that extends into substrate 104 is represented as depth $p_4$ and is of particular interest to process operators who attempt to control trench depth 112 in substrate 104. Optimally, the magnitude of depth $p_4$ should be controlled within a few nanometers (nm). Because trench 112 traverses the mask (photoresist top layer 106), all subsequent layers 108 and the substrate 104, determining the depth which trench 112 extends into substrate 104 necessitates finding both total trench depth $p_2$ and film thickness $p_1$, in addition to knowing intermediate layer(s) thickness $p_3$.

It should be appreciated that generally an excavation process wears away the surfaces of the exposed regions; in the depicted example those regions are represented as regions 102 and 104. As the excavation process progresses, the magnitude for both top layer thickness $p_1$ and trench depth $p_2$ change over time i.e., the value of trench depth $p_2$ increases, while film thickness $p_1$ decreases due to the process wearing away the surfaces of region 104 and top layer 106, respectively. Finding the value of depth $p_4$ is made more difficult because parameters thickness $p_1$ and depth $p_2$ change as the excavation process progresses, but do not change at the same rate. The photoresist of top layer 106 is intended to inhibit the etching while the substrate (104) is worn away at a much faster rate. The total trench depth $p_2 = p_1 + p_3 + p_4$, and $p_2 \geq (p_1 + p_3)$. As trench 112 cuts into region 104, $p_4 > 0$, substrate 104 of region 104 is then etched away until the desired amount of region 104 is worn away i.e., depth $p_4$ reaches a predetermined value and the excavation process is terminated. In this case, the top layer 106 is still intact when $p_4$ reaches its predetermined value, and top layer 106 thickness $p_1$ and trench 112 depth $p_2$ are the quantities which are to be determined. From those values, the depth $p_4$, can be readily calculated for controlling the etch process. It should be understood that process depicted is merely exemplary, and the method could also be applied to a case where all of the top layer and part or all of the intermediate layers 108 are removed.

One aspect of the present invention is its lack of reliance on highly accurate reflectivity measurements of the wafer over a broad range of wavelengths, which are generally only inferred by continuous in-situ monitoring. Therefore, in accordance with one exemplary embodiment of the present invention, data are collected under actual processing conditions using conventional in-situ monitoring techniques. An exemplary in-situ monitoring apparatus for data collection provides spectra from a 10 mm diameter spot on a wafer, usually near the wafer's center. An incident beam passes through a vacuum window, is reflected at normal incidence from the sample, returns through the vacuum window, and is routed to a spectrograph. Typically, each spectrum spans a range of wavelengths λ of 225 nm to 800 nm at a resolution of 0.5 nm. Perry et al. describe a similar collection apparatus in U.S. Pat. No. 6,160,621, which is incorporated herein by reference in its entirety. However, the process of the present invention does not rely on Perry's apparatus nor does it strictly rely on adherence to the above-described in-situ monitoring. Upon reading the present specification, one of ordinary skill in the art will readily understand that a wide variety of known, or heretofore unknown, in-situ monitoring techniques and cooperating devices may be employed from that described herein without deviation for the intended scope of the present invention. Other advantages derived from the present invention relate to the collection of real-time data, in-situ monitoring and control of film thickness, and trench depth determinations will become more apparent with the description of exemplary embodiments of the present invention presented directly below.

Figure 2:
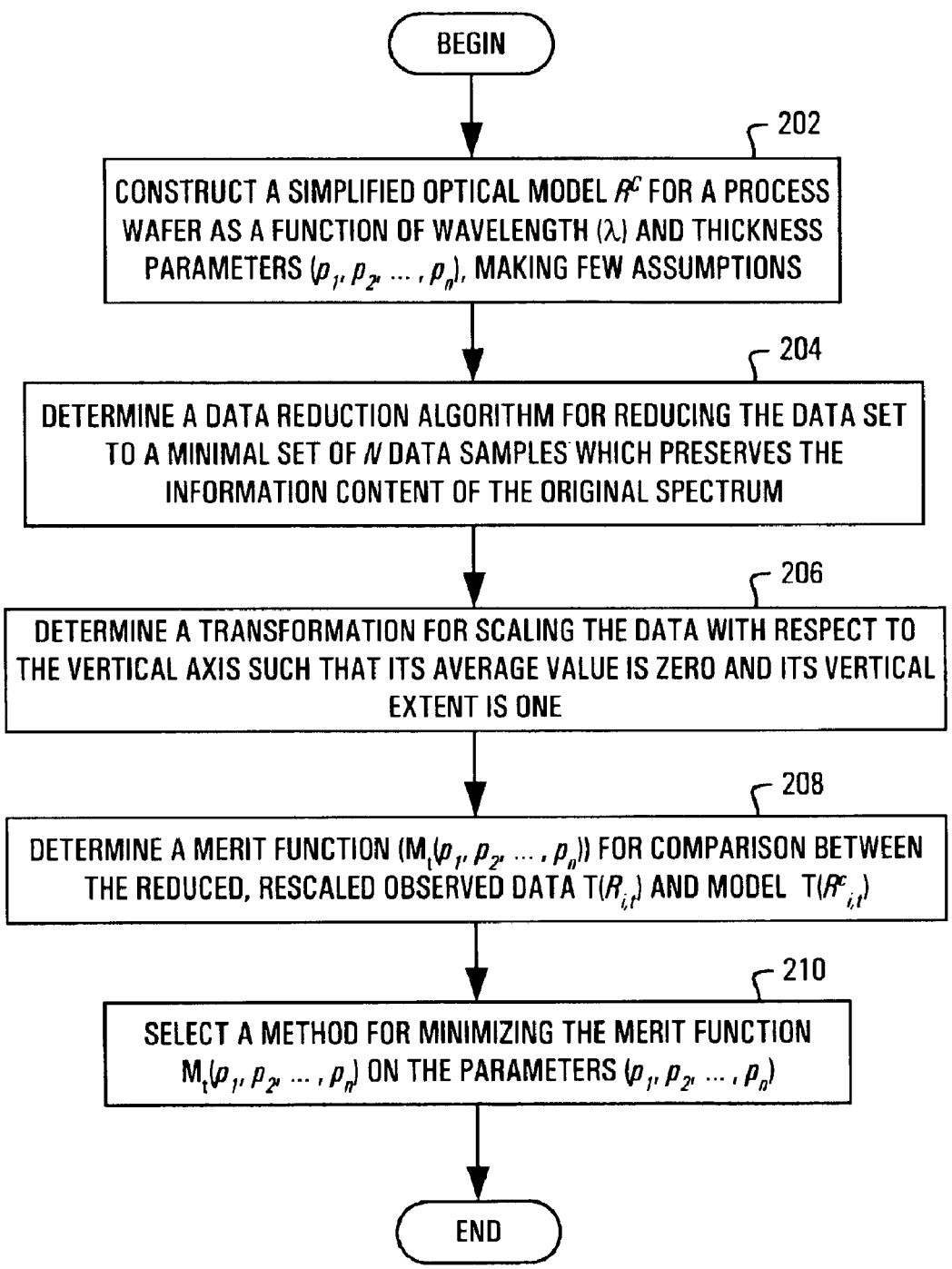
FIG. 2 is a flowchart depicting a generic method for implementing a process for determining film thickness and trench depth in accordance with an exemplary embodiment of the present invention.
Figure 3:
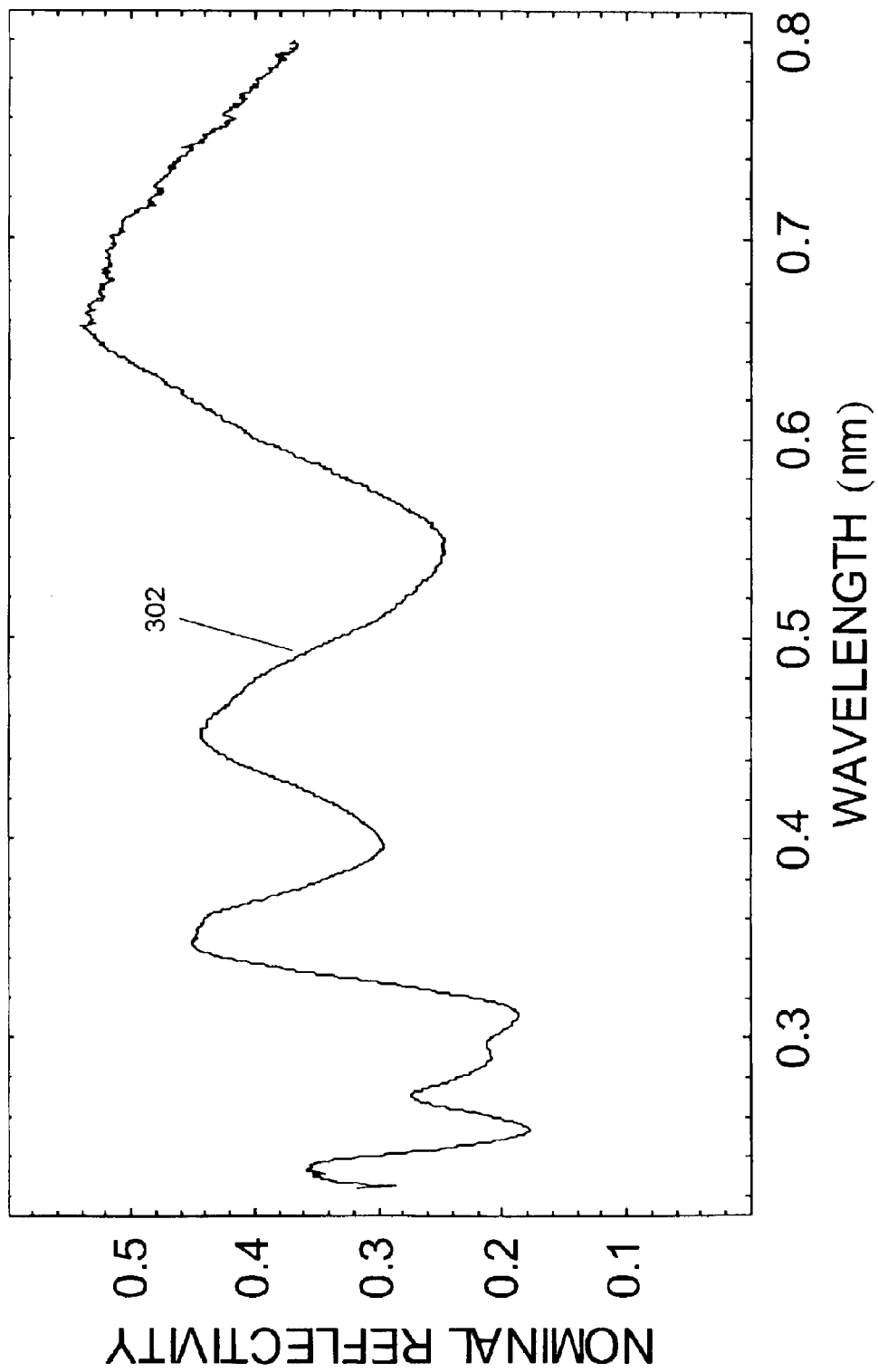
FIG. 3 is a representative nominal reflectivity spectrum taken from in-situ monitoring of a wafer etch.

FIG. 2 is a flowchart depicting a generic method for implementing a process for determining film thickness and trench depth in accordance with an exemplary embodiment of the present invention. Before discussing the method, it should be understood that the exemplary methods presented herein presume the existence of a real-time stream of spectral reflectivity data from the surface being monitored, such as by way of an in-situ monitoring apparatus described above. Additionally, prior to processing the real-time spectral reflectivity data is converted to nominal reflectivity $R(\lambda, t)$, which is then taken as the observed data. The nominal reflectivity is determined from the ratio of a current spectrum to a reference spectrum. The reference spectrum is collected and stored in advance from a bare silicon wafer using the identical processing and monitoring equipment used for processing the production wafer. Bare silicon may be used because these wafers are readily available in semiconductor processing fabrication facilities, and their reflection properties are well characterized. Essentiality the reference spectrum provides spectral intensity information relating to the character of the light wavelength from the illuminating light source. During wafer processing, real-time spectra are collected by the monitoring apparatus at each time step, and the ratio of the current spectrum to the reference spectrum is computed by, for example, the monitoring instrument. The nominal reflectivity is approximately equal to the relative reflectivity of the wafer in process relative to that of bare silicon. Representative spectrum 302 is shown in FIG. 3, which is taken from in-situ monitoring of a wafer etch.

Returning to the discussion of the generic method for implementing a process for determining film thickness and trench depth depicted in FIG. 2, the method begins by constructing a generic optical model $R^c(\lambda, p_1, p_2, \ldots, p_n)$ as a function of wavelength λ and as many parameters ($p_1, p_2, \ldots, p_n$) as are required (step 202). The only assumption made for constructing the optical model for the process wafer is that reflection is proportional to the sum of the reflection from each region ($r_1, r_2, \ldots, r_n$). In accordance with one exemplary embodiment of the present invention, a very simple optical model is used for making comparisons with the observed data requiring only a reduced parameter set ($p_1, p_2, \ldots, p_n$).

An example of a simple optical model for a wafer whose surface is made up of several discrete regions is:

$$R^c(\lambda, p_1, p_2) = \left| ar_1(p_1^a, p_2^a, \ldots) + b\text{Exp}\left(\frac{-4\pi i p_1^b}{-\lambda}\right) r_2(p_2^b, p_3^b, \ldots) + c\text{Exp}\left(\frac{-4\pi i p_1^b}{\lambda}\right) r_3(p_2^c, p_3^c, \ldots) + \ldots \right|^2 \quad (1)$$

In the formula of Equation 1, each region 1, 2, 3... is represented by a term in the equation. In each term, the letter a, b, c, . . . represents the fraction of the surface occupied by that region. The terms $r_1$, etc., are the reflectances of the various regions, each comprising a single stack, and these can be computed using the standard formalism for calculating the reflection coefficient of a multilayer stack. Details about these calculations can be found, for example, in Ellipsometry and Polarized Light (Azzam and Bashara, pp. 332–340, Elsevier, 1987), which is incorporated herein in its entirety. The parameters p within these terms are the refractive indices and thicknesses of the various constituent layers. For all but the first term, the vertical distance between the top of the first layer and the top of the layer in question enters as a parameter (e.g., $p_1^b$ in the second term) to account for the phase shift between reflection from the various zones.

The use of a simple optical model for accurately determining film thickness and trench depth is possible because, unlike prior art optical models, the present method eliminates the necessity for computing a spectrum which precisely matches the observed spectra. Therefore, superior film thickness and trench depth thickness results are achieved using compromised reflectivity data, such as might be expected from a real-time in-situ monitoring environment, in addition to utilizing a highly simplified optical model.

The reflectivity of the surface is then:

$$R^C(\lambda, p_1, p_2) = \left| ar_1(p_1) + b\text{Exp}\left(\frac{-4\pi i p}{\lambda}\right) r_2 \right|^2 \qquad (2)$$

In the exemplary generic model disclosed above, and as used hereinafter, a parameter p refers to any property, characteristic or attribute that affects the reflective properties of a region of the wafer in any calculable way. As used to describe the exemplary embodiments of the present invention, $p_1$ and $p_2$ are the spatial parameters (depth and thickness) of the STI structure for the respective regions on the wafer. Accordingly, $p_1$ refers to a spatial parameter unique to a structure in one region, while $p_2$ refers to a spatial parameter unique to a separate structure in a second region. a and b are weighting coefficients that describe the relative contribution expected from each region and are an estimate of the relative portions of the respective region to the production wafer such that (a+b=1).

It should be understood that while the present exemplary embodiments describe the invention with regard to an exemplary wafer comprising two discrete regions, and having a corresponding depth or thickness parameter for each region, the parameters might instead be indicative of any other property, characteristic or attribute that affects the reflective properties of a region without departing from the intended scope or spirit of the present invention such as a refractive index of the regions. Moreover, the optical model may be extended for calculating the reflectivity of a wafer having more than two discrete regions by increasing the number of parameters correspondingly and, if necessary, providing an equivalent number of additional weighting coefficients.

With more specific regard to the exemplary generic model disclosed above, the present invention will now be described with reference to an exemplary STI structure having two discrete regions as depicted in FIG. 1 above. For the purposes of describing the present invention, the first region (113) is that of multilayer dielectric stack 102 and the second region (114) is that of the wafer's substrate 104, in this case, silicon. Here $r_1$ and $r_2$ are the reflection coefficients of the two regions 113 and 114, respectively. $p_1$ is the thickness of top layer 106 and $p_2$ is the separation between the top layers of regions 113 and 114. a and b are weighting coefficients. The reflection coefficient $r_2$ for region 114 is simply the reflectivity of substrate 104, or silicon, which can be computed from Fresnel's equation using the real and imaginary parts n and k of the refractive index of silicon:

$$r = \frac{n - ik - 1}{n - ik + 1} \qquad (3)$$

The reflection coefficient for region 113 can be computed using the standard formalism for calculating the reflection coefficient of a multilayer stack. Details about these calculations can be found, for example, in Ellipsometry and Polarized Light (Azzam and Bashara, pp. 332–340, Elsevier, 1987), which is incorporated herein in its entirety. The weighting coefficients a and b (b=1−a) are estimates of the relative portions of the respective areas on the production wafer. For instance, one of a and b being first region 113, or dielectric stack 102, and the other of a and b being second region 114, or the wafer's substrate 104. Equation 2, evaluated at a series of wavelengths corresponding to the data, comprises the optical model.

Figure 4:
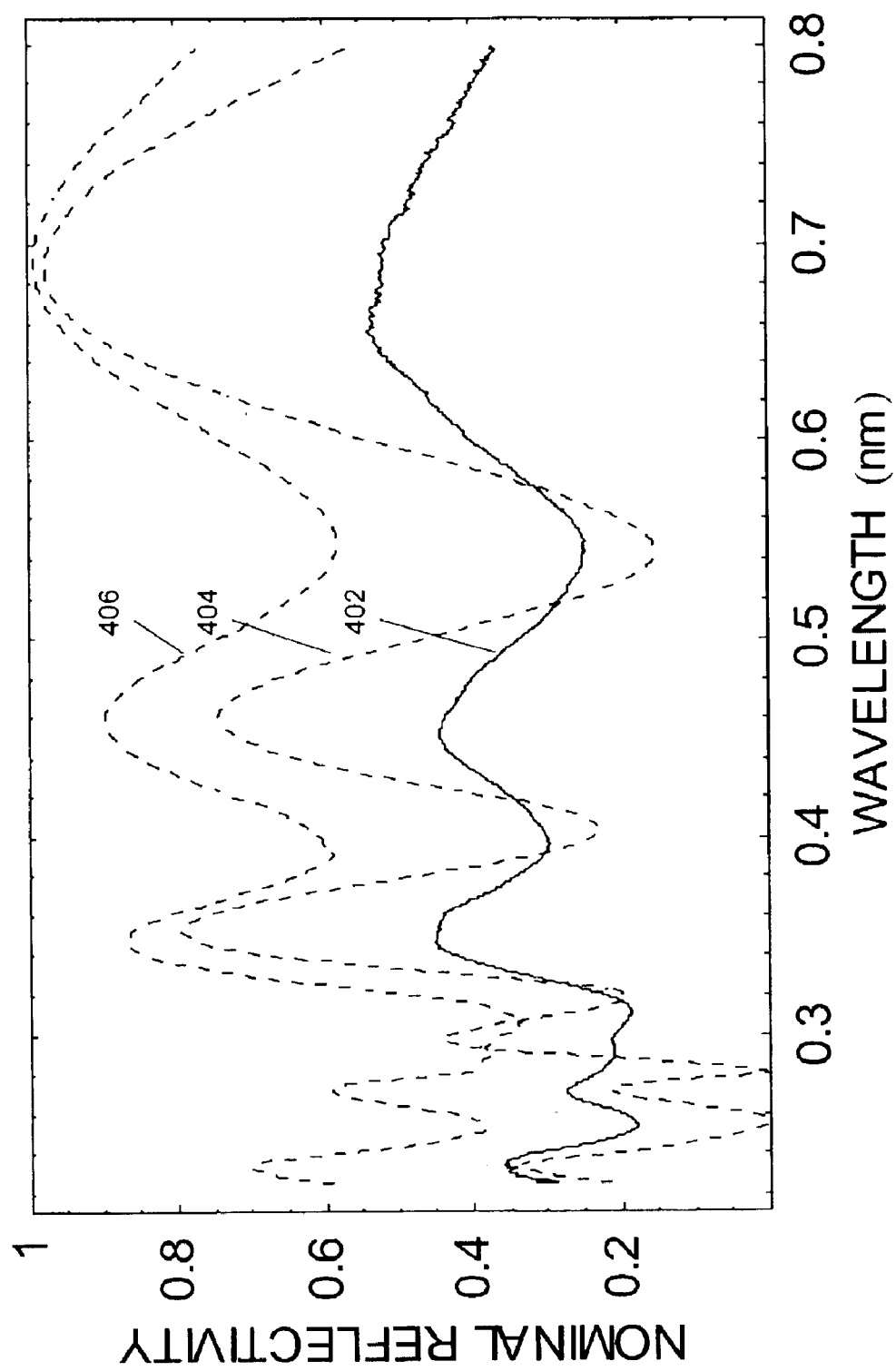

The optical model from Equation 2 contains three unknown parameters, a, $p_1$ and $p_2$, assuming the optical constants of each of the constituent materials are known. The optical model in this form does not accurately predict the observed nominal reflectivity of the structure. This discrepancy between the model and observed data can be more readily understood from a plot of the model evaluated for the correct values of $p_1$ and $p_2$ superimposed on the observed spectrum. FIG. 4 shows the optical model described by Equation 2 evaluated for the correct values of $p_1$=167 nm and $p_2$=690 nm and two different values of the parameter a. Curve 404 shows the model evaluated for the optimum value of a=0.779 as determined by fitting. Additionally, curve 406 shows the model evaluated for the optimum value of a=0.25. In either case, the large residual error between observed data 402 and the calculated models (404 and 406) indicates that it is improbable that a 3-parameter fit on parameters $p_1$, $p_2$ would have converged to the right values. Hence, the presently described optical model is too simple to be used with the prior art matching methods for obtaining accurate thickness results.

Therefore, in accordance with an exemplary embodiment of the present invention, the observed spectrum to a calculated spectrum comparison utilizes a method which does away with the requirement of a substantially good fit between observed and calculated spectra. Thus, the comparison technique described below uses only the simplified optical model described above, and observed data from real-time in-situ monitoring of a process wafer. The first step in matching the observed data to an optical model is to reduce the data to a minimal set which facilitates faster computations while preserving the information content of the original nominal reflectivity spectrum (step 204). The observed nominal reflectivity spectra are typically reported by the monitoring instrument as a series of measurements on a regularly spaced wavelength grid. With regard to the exemplary monitoring apparatus described above, each spectrum consists of wavelengths λ between 225 nm and 800 nm in which measurements are taken at (or averaged across) a resolution of 0.5 nm, yielding 1151 discrete data points of nominal reflectivity spectral data taken at each sample time t. It is not necessary to compare the observed and modeled spectra at each point in order to assess the degree of agreement between the observed and computed spectra. Over a small enough wavelength interval, the reflectivity varies slowly enough that comparison at a single point is sufficient. Comparison at additional points increases the computation time needed without providing any additional accuracy in the film thickness and trench depth results. Therefore, use of components of an exemplary embodiment of the present invention is a way to compute from the observed nominal reflectivity spectrum a minimal set of values for comparison without compromising the results. This will preferentially entail partitioning the spectrum into wavelength intervals over which the spectrum can be considered slowly varying, and making a single comparison for each such wavelength interval.

One can see in FIG. 4 that the size of a wavelength interval over which the observed nominal reflectivity spectrum 402 can be considered slowly varying is smaller in the short-wavelength end of the spectrum. This is because the physically relevant parameter is the ratio of some characteristic feature dimension on the wafer to the wavelength. Accordingly, we describe an exemplary method of reducing the observed spectra to an optimal reduced set which more nearly optimizes the number of points which must be chosen. First we pick a spectrum which is representative of the data to be encountered during processing. If the spectra vary in their complexity, e.g., throughout the course of processing or among samples, then a spectrum with the greatest complexity should be chosen. Then we pick a number of partitions N to try, where N is much smaller that the original number but still expected to be large enough to capture the essential shape of each spectrum. Then we compute the partition boundaries. These are a-set of N+1 wavelengths i=1, . . . , N+1, which includes the endpoints of the original list (225 nm and 800 nm) and N-1 intermediate wavelengths chosen so that the reciprocals of the N+1 $\lambda_i$ are approximately evenly spaced, within the accuracy permitted by the wavelength resolution. The endpoints for the partitions may be chosen using any method that yields reciprocals that are approximately evenly distributed. The wavelength and reflectivity data within each partitioned region is then averaged to obtain a single pair (wavelength, reflectivity) representative of the respective region. The plot of the reduced data set is then plotted on the same axes as the full spectrum (FIG. 4). If interpolation between the points of the reduced spectrum produces a spectrum with substantially the same shape as the full spectrum, as is the case in this example, then N is sufficiently large. It is not necessary or even desirable to find the smallest possible value of N, for if N is too small, then there is a risk that the method will fail, and considerable reduction in the computational load is generally achievable without approaching this limit.

Having determined a value for N, the original data set is reduced to a minimally sized data set with N members.

Figure 5:
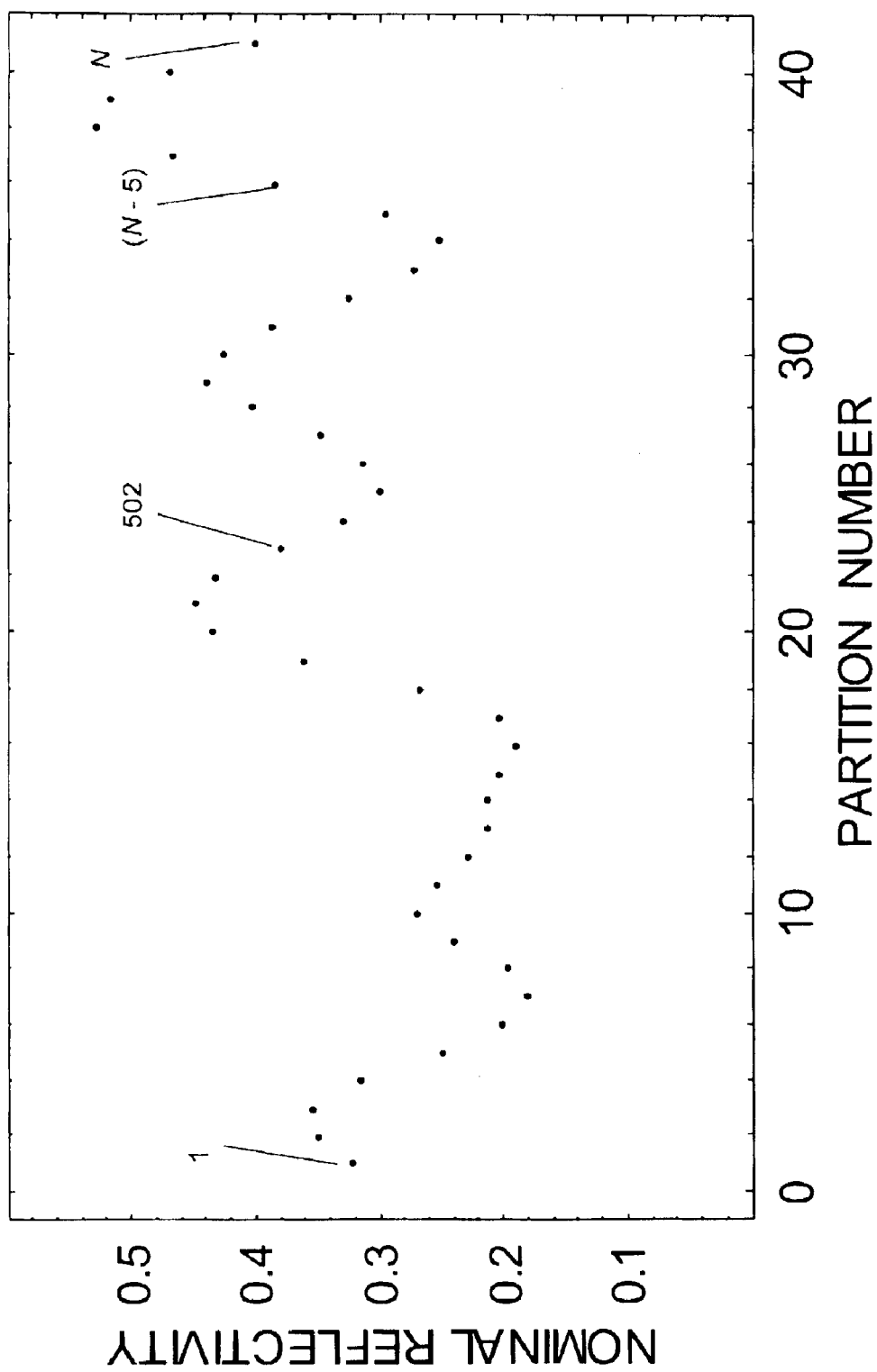
FIG. 5 depicts 41 discrete reflectivity values of nominal reflectivity spectrum, one for each of the 41 partitioned regions of the reflectivity spectrum in accordance with an exemplary embodiment of the present invention.

The effect of partitioning the data set can be seen from FIG. 5. In FIG. 5, vector 502, corresponding to nominal reflectivity spectrum 302 in FIG. 3, is shown as 41 discrete reflectivity values, one for each of the N partitioned regions over the reflectivity spectrum. As described immediately above, a single data point is computed for each partition by averaging the nominal reflectivity over the entire region. After the data reduction transformation, at each time step t the data is in the form of a vector $R_{i,t}$, where i is the index corresponding to wavelength, and runs from 1 to the number of partitions, N (41 partitions are shown in FIG. 5). Thus, the spectral data for fitting can now be thought of as a list R of length N without explicit reference to wavelength.

Next, the data is transformed with respect to the vertical axis such that the average value of the data is zero, and the vertical extent of the data is one (step 206). The vertical range of the data provides a convenient scale that can be imposed on the model results rather than trying to calculate it. By transforming both the observed data and calculated model in such a way that their vertical extent and spectrally averaged values coincide, large errors in both the data and the model can be tolerated and still find a deep minimum in the appropriately constructed merit function at the correct values of the parameters. The transformed data is then:

$$\tilde{R}_{i,t} \equiv T(R_{i,t}) = \frac{R_{i,t} - \frac{1}{N}\sum_{j=1}^{N} R_{j,t}}{\text{Min}(R_{i,t}) - \text{Max}(R_{i,t})} \quad (4)$$

Re-scaling and averaging the data involves first finding the vertical extent of the data for a particular spectrum at each time step t. From the N samples, the least and greatest values for $R_i$, are found from the N reflectivity sample, i ranges from 1 to N. These are the Min($R_i$) and Max($R_i$). The vertical extent of the data, Max($R_i$)–Min($R_i$), establishes the vertical range for rescaling the observed data and the calculated model, which relaxes the requirement of accurately calculating the reflectivity. Every spectrum, whether a calculated spectrum or an observed spectrum, is scaled according to the maximum and minimum $R_i$ values contained within it. The method is most successful if interference minima and maxima occur in every spectrum, which will be more likely if the data includes a wide range of wavelengths, and especially the ultraviolet wavelengths, generally between 200 nm and 400 nm.

Figure 6:
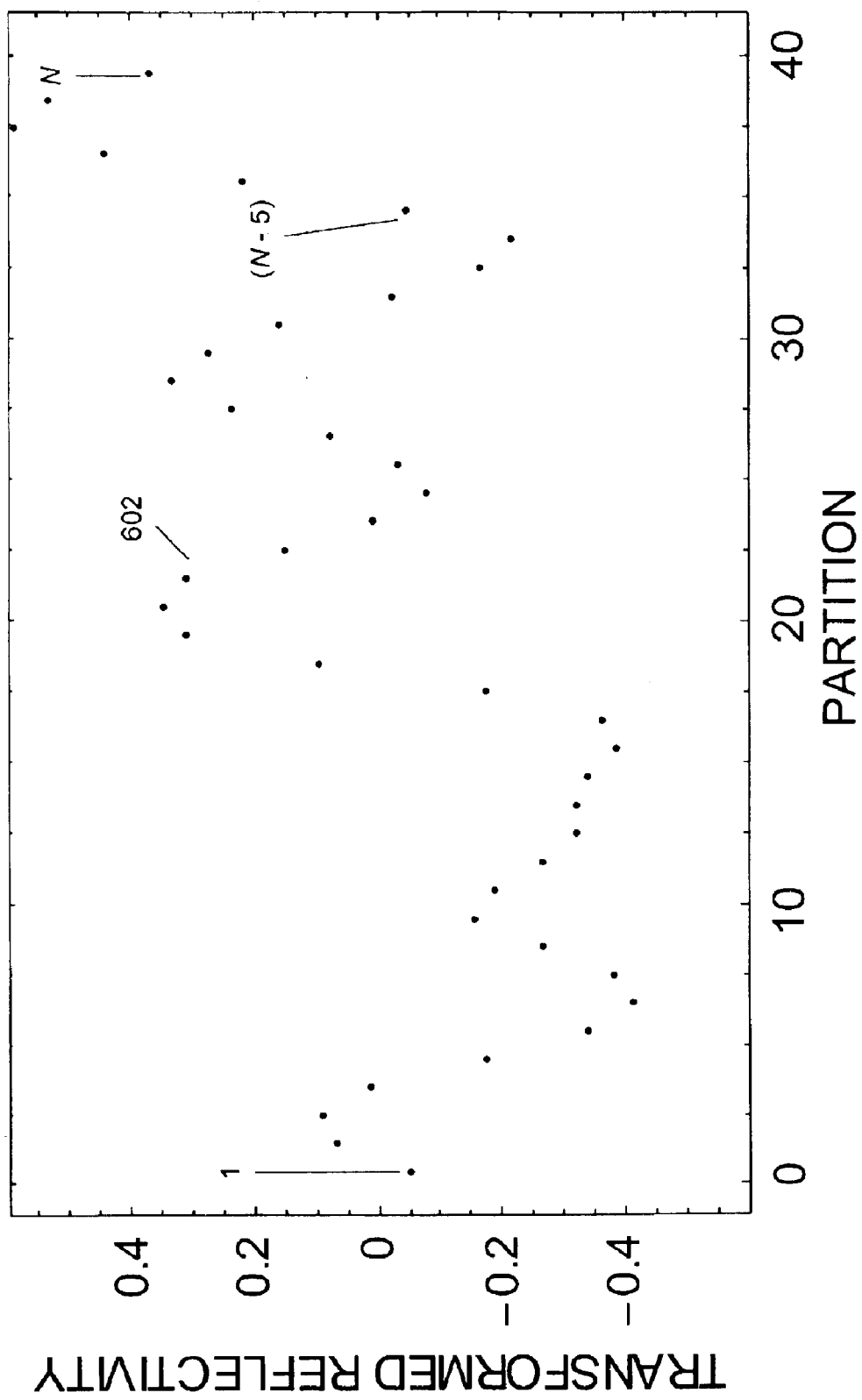
FIG. 6 is a diagram depicting a transformed reflectivity vector, $T(R_{i,t})$, which shows the 41 discrete reflectivity values rescaled such that the vertical extent and spectrally averaged values coincide with a transformed model vector, $T(R^c_{i,t})$, in accordance with an exemplary embodiment of the present invention.

FIG. 6 is a diagram depicting vector 602, T($R_{i,t}$), which corresponds to nominal reflectivity spectrum 302 in FIG. 3, which shows the 41 discrete reflectivity values as they would appear after the final transformation. Vector 602 has a vertical extent of approximately 1 and an average value across the spectrum of 0.

With the data properly transformed, a figure-of-merit function or merit function $M_t(p_1, p_2, \ldots, p_n)$ is used for comparison between the observed data $R^{obs}$ and the model $R^c$ (step 210). As those of ordinary skill in the art will readily understand, a merit function measures the agreement between observed data and the model with a particular choice of parameters. The merit function is designed and arranged such that close agreement between the observed data and the model will be represented by a small value. The minimum in the merit function is determined by adjusting the parameters of the model, thereby yielding best-fit parameters and may take the form of any standard numerical techniques known in the prior art, such as the Levenburg-Marquardt method. Below is described a generic merit function in accordance with an exemplary embodiment of the present invention.

$$M_i(p_1, p_2, \ldots p_n) = \sum_{j=1}^{N} (T[R_j^c(p_1, p_2)] - T[R_j])^2 \text{ with} \quad (5)$$

$$T(R_i) = \frac{R_i - \frac{1}{N}\sum_{j=1}^{N} R_j}{\text{Max}(R_i) - \text{Min}(R_i)} \quad (6)$$

Finally, minimization of the merit function may proceed. In accordance with an exemplary embodiment of the present invention, the model can be computed in advance to create a lookup table which is searched exhaustively at run time. This is possible using the present process because the parameter space is only two-dimensional i.e., $p_1$ and $p_2$. The table is made up of the set of vectors $T[R^c_{j,t}(p_1, p_2)]$ for every possible trench depth and layer thickness pair on 1 nm intervals over the full range of expected values. Agreement between the observed data and the model can be found by exhaustively searching the entire two-dimensional parameter space instead of by numerical minimization techniques. This alternative is superior to standard numerical minimization techniques of the prior art because the results do not depend on an initial guess.

Figure 7A:
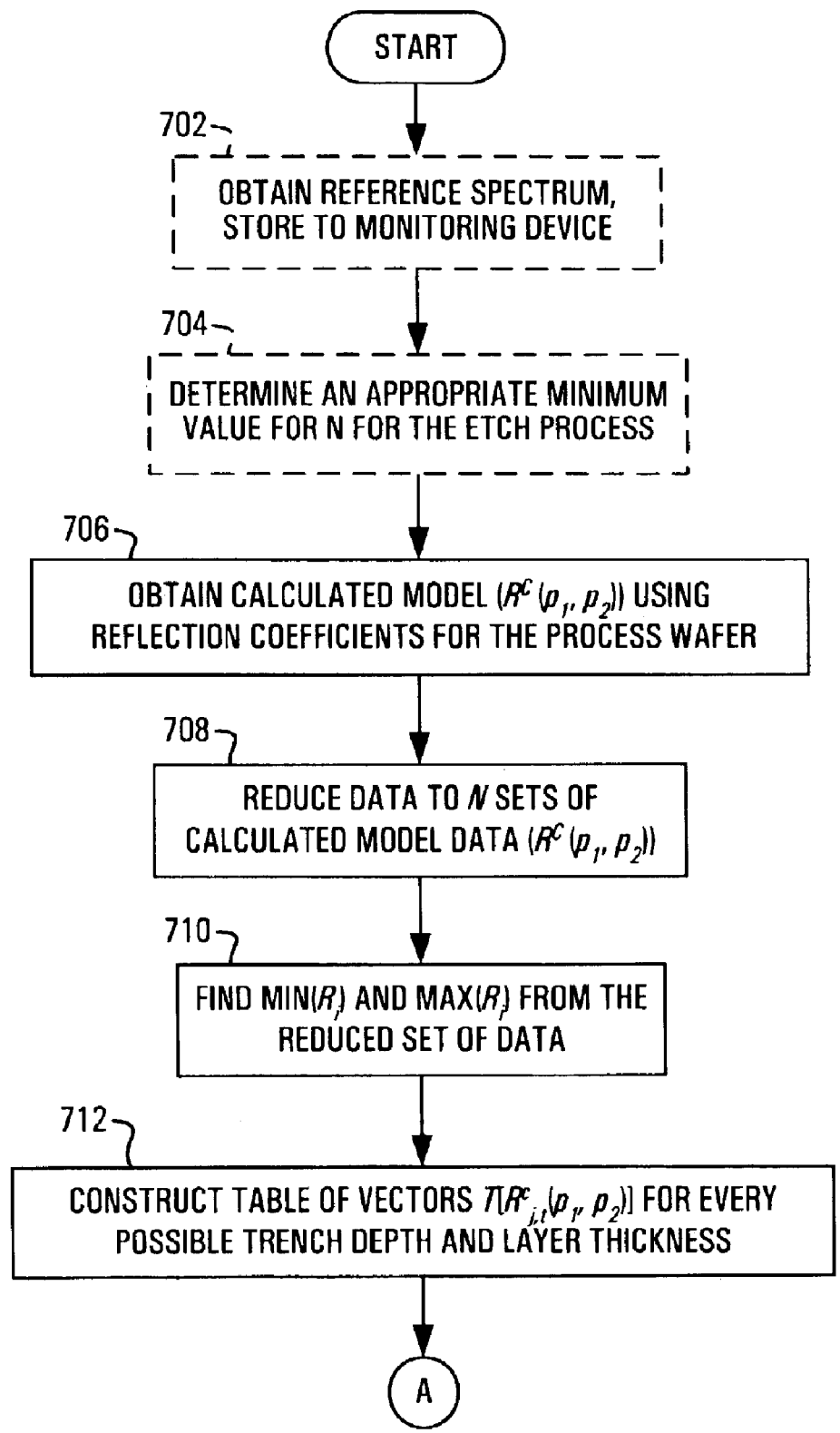
FIGS. 7A and 7B depict a flowchart of a process for in-situ monitoring for film thickness and trench depth parameters and controlling an etch process in accordance with an exemplary embodiment of the present invention.
Figure 7B:
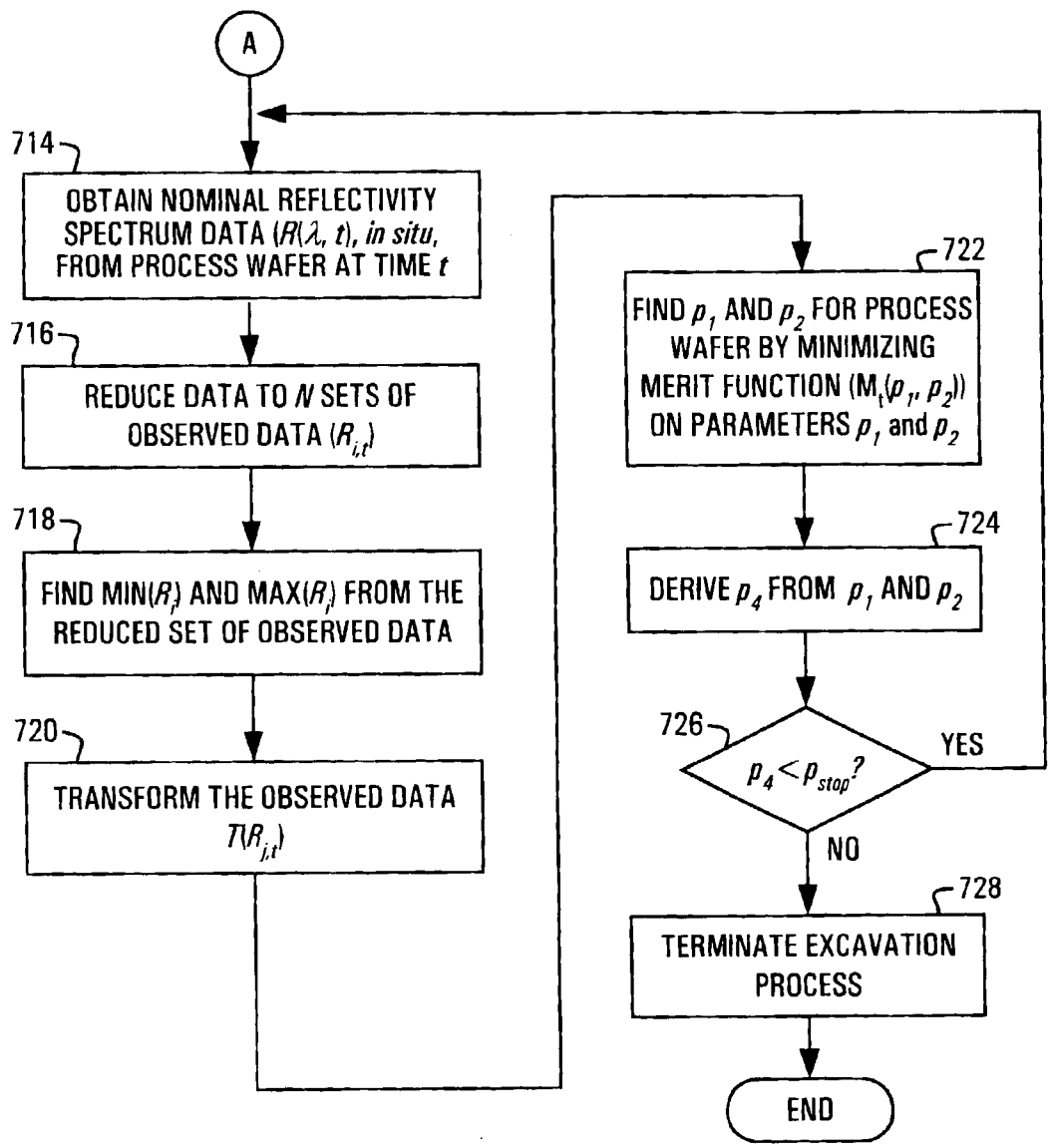

FIGS. 7A and 7B depict a flowchart of a process for in-situ monitoring and controlling film thickness and trench depth in accordance with an exemplary embodiment of the present invention. Results from the depicted process are achieved in real-time during wafer processing using the generic implementation method described above, and will be described below in conjunction with the STI structure illustrated in FIG. 1. The flowchart is divided into two sections, that shown in FIG. 7A which addresses steps that should be completed prior to processing the wafer, and FIG. 7B which shows the real-time processing steps of the present invention.

As mentioned previously, prior to actually processing the wafer, several bits of data should be gathered for the particular wafer process to be performed. The data for these steps should be obtained using the etch chamber and monitoring device employed in processing subsequent similar production wafers. The blocks in FIG. 7A representing these data acquisition steps are depicted as broken lines to signify that the data obtained therein remain valid for any subsequent processing on similar production wafers using the chamber and measurement apparatus. However, it should be understood that if the accuracy of thickness results obtained by the present method are questionable, i.e., something relating to the etch process or production wafer may have changed, then these data should be reacquired prior to processing other production wafers.

Initially, a reference spectrum is obtained from a silicon wafer using the etch chamber and in-situ monitoring device to be employed in the production processing of wafers (step 702). The reference spectrum is then stored in the monitoring device for converting the real-time spectral reflectivity data obtained during production processing into nominal reflectivity $R(\lambda, t)$. Additionally, prior to beginning the etch process, a value for N should be determined for reducing the data to a minimal set of data that preserves the information content of the original nominal reflectivity spectrum (step 704). Generally, N is determined such that shape of the reduced spectrum does not differ substantially from the shape of the original spectrum. N may be determined empirically by analyzing spectral data obtained by processing a production wafer, or might instead be determined by analyzing calculated data using an optical model constructed for the production wafer.

Here it should be appreciated that as a practical matter, the thickness determination and control process may proceed in one of two alternate flows in accordance with exemplary embodiments of the present invention. The first alternative involves constructing the optical model in advance and then creating a lookup table consisting of vectors $T[R^c_{j,t}(p_1, p_2)]$ for every possible trench depth and layer thickness pair expected for the etch process. This table can then be exhaustively searched for agreement with the observed data. The second alternative is to construct the optical model in advance, but evaluate it on the fly by adjusting the parameter values to yield the best-fit parameters for observed data taken at any time step, t. Here, the optical model is compared to the observed data using any standard numerical technique. The first approach is somewhat less time consuming, but either approach achieves superior thickness results in a run time environment. The differences in the two approaches will be emphasized throughout the discussion below.

In either approach, the optical model $R^c(p_1, p_2)$ is obtained for the wafer structure to be evaluated, such as Equation 2 above, using the reflection coefficients for the particular type of STI structure to be processed (step 706). In the first approach, a set of vectors $T[R^c_{j,t}(p_1, p_2)]$ for every possible trench depth and layer thickness within the expected range is compiled into a lookup table. Thus, for every trench depth and layer thickness pair, the model data is reduced to N values of averaged reflectivity data (step 708), and then the $Min(R_i)$ and $Max(R_i)$ (least and greatest values for $R_i$) are found for the N reflectivity samples for each parameter pair. The model data associated with each depth and layer thickness pair is then transformed point-by-point by a linear transformation to yield a vector whose average is zero and whose range (defined as the maximum value minus the minimum value) is one (step 710). Equation 4, described above, is an exemplary algorithm that may be used for this purpose. The resulting vectors $T[R^c_{j,t}(p_1, p_2)]$ are consolidated in a lookup table which are indexed to their $p_1$ and $p_2$ values (step 712).

Turning now to FIG. 7B, the etch process begins on the subject process wafer and reflectivity data is monitored, in-situ, from the wafer's surface at time step t (step 714). The nominal reflectivity $R(\lambda, t)$ is automatically computed from the spectra collected by the instrument using the reference spectrum. Next, the data set produced by the instrument is reduced to N data points (step 716). This step may be accomplished internally by the monitoring device but might instead be a function of the external data processor. Next, the $Max(R_{i,t})$ and $Min(R_{i,t})$ values for the N sets of $R_{i,t}$ are found (step 718) and used to transform the observed data $T(R_{j,t})$ such that its vertical extent and spectrally averaged value coincide with the calculated model $(T(R^c_{j,t}(p_1, p_2))$ using, for example, Equation 4 above (step 720). Recall that the vector data for the lookup table have been transformed similarly prior to entry into the table.

If, on the other hand, a lookup table is not used, then the optical model $R^c(\lambda, p_1, p_2, \ldots, p_n)$ must be evaluated at each of N wavelengths to produce the list $R^c(p_1, p_2)$. This list is transformed as described above with regard to steps 708 and 710. Once transformed, the model data is compared to the observed data for the $t_{th}$ time step. This is accomplished using a specific form of the generic merit function described above in Equation 5 for the two parameters $p_1$ and $p_2$, i.e., the merit function is in the form $M_r(p_1, p_2)$. The magnitude for both top layer thickness $p_1$ and trench depth $p_2$ are determined for wafer state at the $t^{th}$ time step of the etch process by minimizing merit function $M_1(p_1, p_2)$ on parameters $p_1$ and $p_2$ (step 722). The minimization may be performed using a standard numerical technique, such as the Levenburg-Marquardt method.

Conversely, if a lookup table has been created in advance, then the two-dimensional parameter space is exhaustively searched for parameters $p_1$ and $p_2$ at run time. As mentioned above with regard to step 712, the lookup table is made up of the set of vectors $T[R^c_{j,t}(p_1, p_2)]$ for every possible trench depth and layer thickness pair over the full range of expected values. The range parametric values are incremented at some non-arbitrary interval, for instance 1 nm, which provides the resolution necessary for controlling the etch process.

Figure 8:
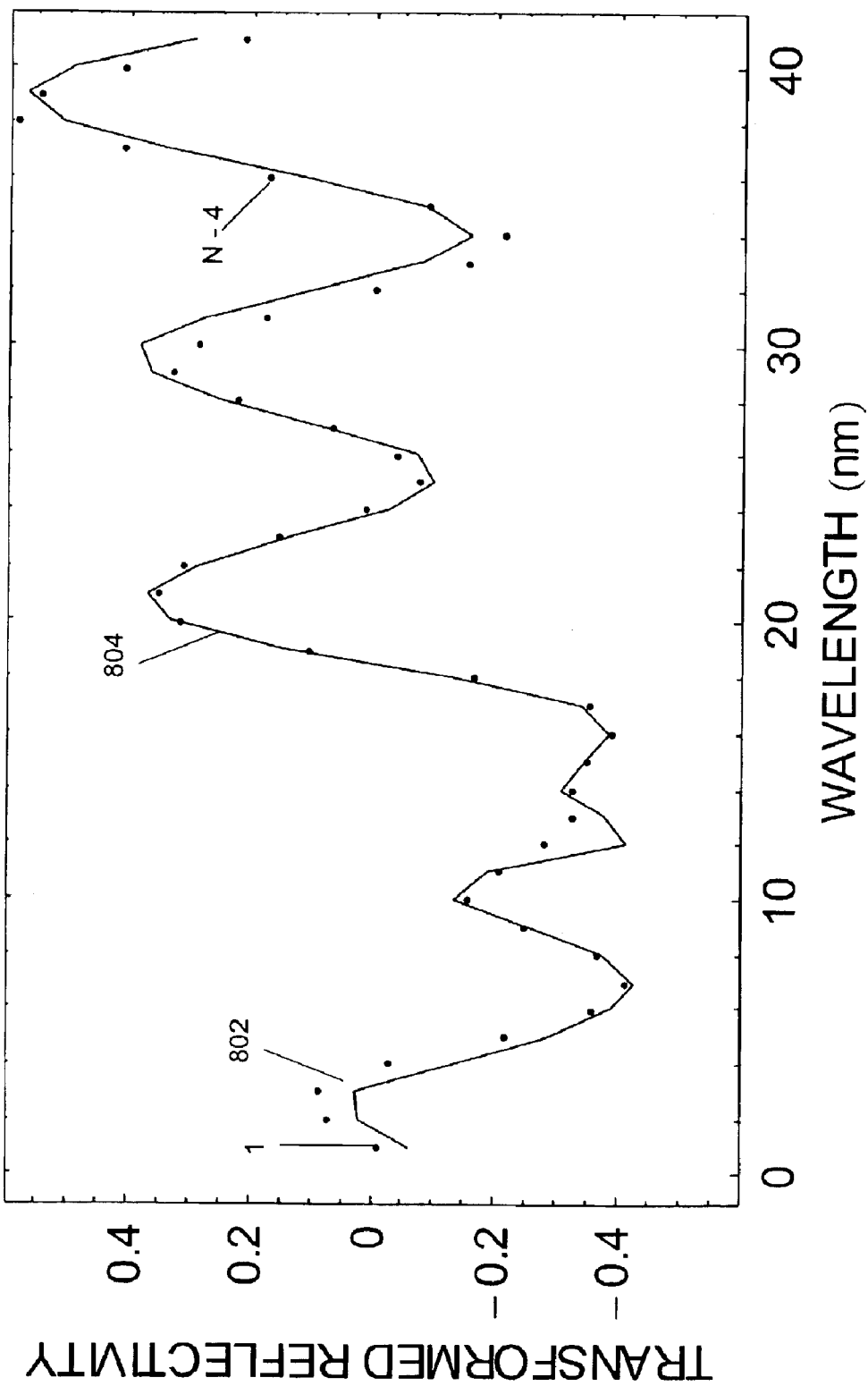
FIG. 8 is a diagram depicting the result of a two parameter search on film thickness and trench depth parameters $p_1$ and $p_2$ in accordance with an exemplary embodiment of the present invention.

FIG. 8 is a diagram depicting the result of the 2-parameter search on $p_1$ and $p_2$ for the spectrum 602 shown in FIG. 6 above. There, the 41 discrete values representing $T(R_{i,t})$ 802 are overlaid by vector $T[R^c_{j,t}(p_1,p_2)]$ 804.

Having obtained the correct values for top layer thickness $p_1$ and trench depth $p_2$, the depth portion of trench 112 that extends into substrate 110 (depth $p_4$) may be found by $p_4=p_2-(p_1+p_3)$, where $p_3$ is the known thickness of intermediate layer(s) 108 (step 724). Depth $p_4$ is compared to the stop depth, $p_{stop}$, which represents the target depth of the excavation in substrate 110. If depth $p_4<p_{stop}$, the process reverts to step 714 for obtaining a new nominal reflectivity $R(\lambda, t)$ at the next time step t. The process then iterates through steps 716 through 726 until depth $p_4 \geq p_{stop}$, and the excavation process is terminated (step 728).

Figure 9:
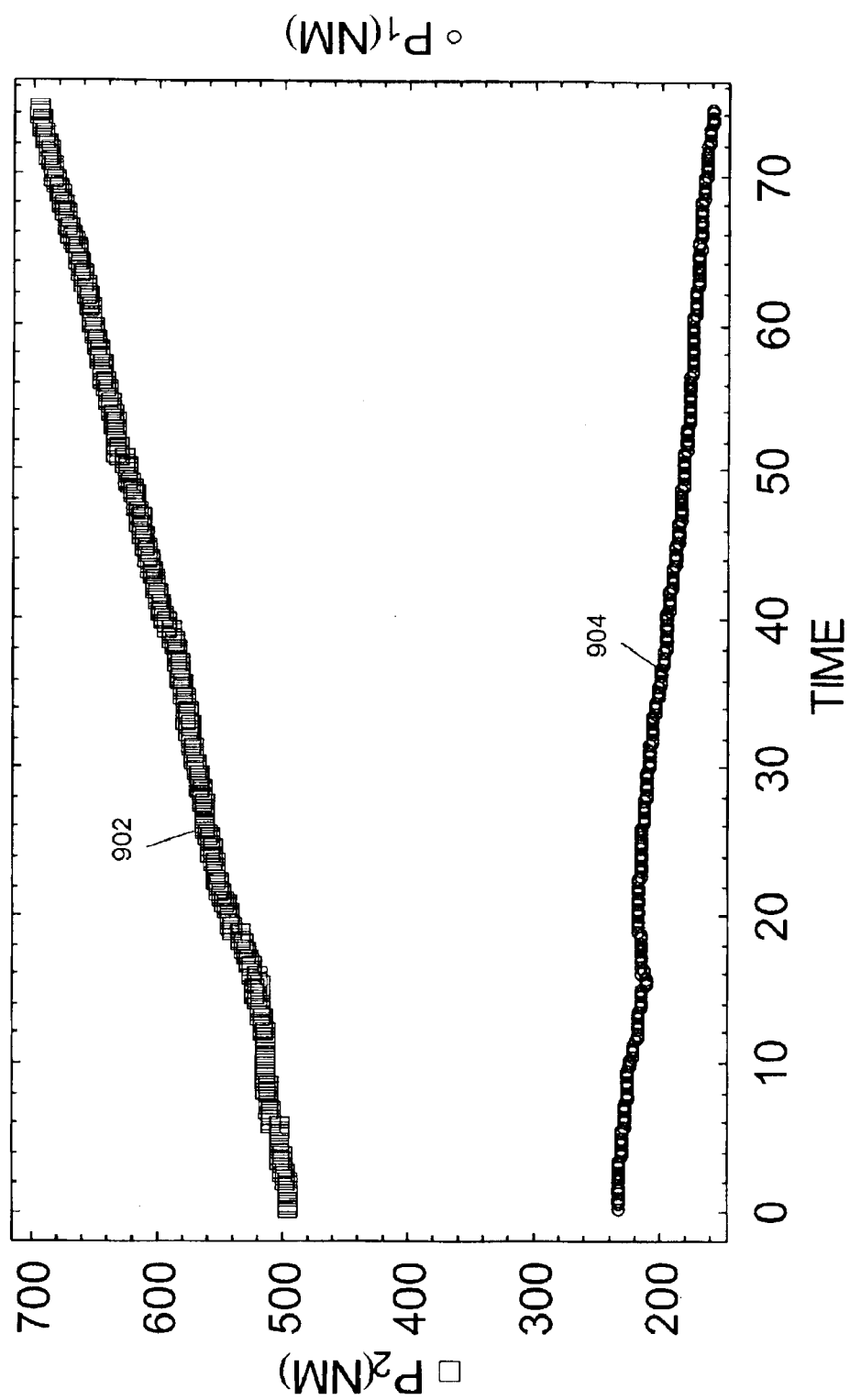
FIG. 9 is a diagram depicting values for top layer thickness $p_1$ and trench depth $p_2$ derived in accordance with embodiments of the present invention and plotted at time steps t.
Figure 10:
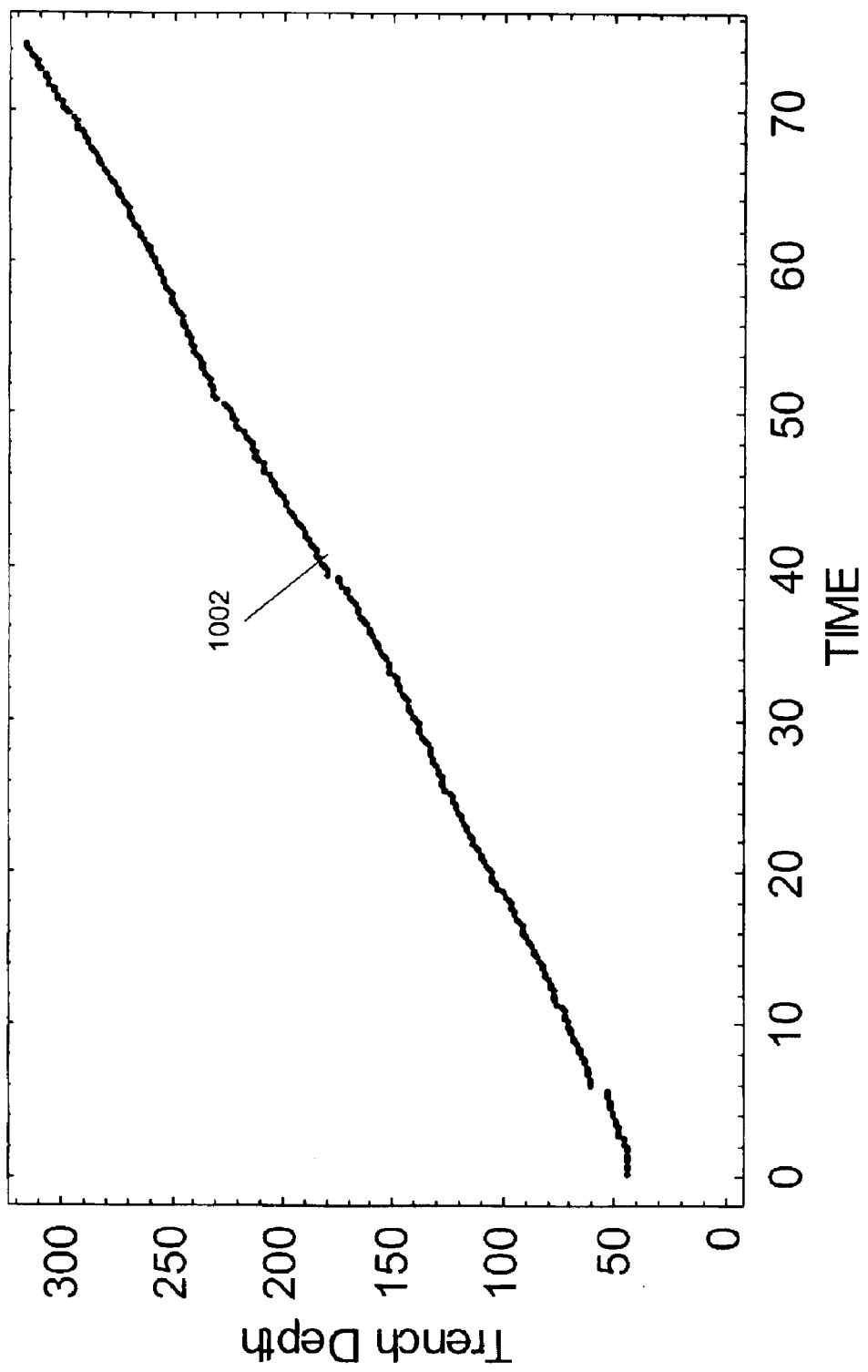
FIG. 10 depicts a plot of trench depth in silicon $p_4$ derived in accordance with embodiments of the present invention and plotted over the same time interval as FIG. 9.

Turning now to FIG. 9, top layer thickness $p_1$ 802 and trench depth $p_2$ 804 are depicted with respect to time. Notice that, as the etch process proceeds through time steps t, trench depth $p_2$ 804 increases while top layer thickness $p_1$ 802 decreases, as should be expected. The pair of parameters calculated at each time step t is independent of the prior values, so the smooth variation seen in these plots indicates that the search is indeed returning the correct value because each value smoothly transitions between time steps. FIG. 10 depicts a plot of trench depth in silicon $p_4$ 1002 over the same time interval. Recalling that depth $p_4$ is derived from thickness $p_1$ 802 and depth $p_2$ 804 and known thickness of intermediate layer(s) 108, it is apparent that the values for silicon depth $p_4$ are also correct because they also smoothly transition from one value to the next between time steps.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated. The foregoing is and various modifications can be made by those skilled in the art.

What is claimed is:

1. A method for determining a value for at least one parameter associated with a wafer comprising:
    receiving observed reflectivity data from a surface of a wafer;
    obtaining calculated reflectivity data for the wafer, said calculated reflectivity data being a function of at least one parameter;
    transforming one of the observed reflectivity data and the calculated reflectivity data;
    transforming the other of the observed reflectivity data and the calculated reflectivity data to coincide with the transformed one of the observed reflectivity data and the calculated reflectivity data;
    finding agreement between the transformed one of the observed reflectivity data and the calculated reflectivity data, and the transformed other of the observed reflectivity data and the calculated reflectivity data on the at least one parameter; and
    determining a value for the at least one parameter based on the agreement.

2. The method recited in claim 1 above, wherein the observed reflectivity data is a ratio of spectral reflectivity of the surface of the wafer and a reference reflectivity spectrum.

3. The method recited in claim 1 above, wherein the observed reflectivity data is associated with a state of the surface of the wafer.

4. The method recited in claim 3 above, wherein transforming one of the observed reflectivity data and the calculated reflectivity data further comprises:
    finding a vertical extent of the one of the observed reflectivity data and the calculated reflectivity data; and
    scaling the one of the observed reflectivity data and the calculated reflectivity data based on the vertical extent of the one of the observed reflectivity data and the calculated reflectivity data.

5. The method recited in claim 4 above further comprises:
    averaging the scaled one of the observed reflectivity data and the calculated reflectivity data.

6. The method recited in claim 5 above, wherein transforming the other of the observed reflectivity data and the calculated reflectivity data further comprises:
    finding a vertical extent of the other of the observed reflectivity data and the calculated reflectivity data; and
    scaling the other of the observed reflectivity data and the calculated reflectivity data based on the vertical extent of the other of the observed reflectivity data and the calculated reflectivity data.

7. The method recited in claim 6 above further comprises:
    averaging the scaled other of the observed reflectivity data and the calculated reflectivity data.

8. The method recited in claim 7, wherein the scaled one of the observed reflectivity data and the calculated reflectivity data coincides with the scaled other of the observed reflectivity data and the calculated reflectivity data.

9. The method recited in claim 8, wherein a vertical extent of the scaled one of the observed reflectivity data and the calculated reflectivity data has a value of one and a vertical extent of the other of the observed reflectivity data and the calculated reflectivity data also has a value of one.

10. The method recited in claim 7 above, wherein the averaged, scaled one of the observed reflectivity data and the calculated reflectivity data coincides with the averaged, scaled other of the observed reflectivity data and the calculated reflectivity data.

11. The method recited in claim 10 above, wherein an average of the averaged, scaled one of the observed reflectivity data and the calculated reflectivity data has an approximate value of zero and an average of the averaged, scaled other of the observed reflectivity data and the calculated reflectivity data also has an approximate value of zero.

12. The method recited in claim 7 above, wherein finding agreement between the transformed one of the observed reflectivity data and the calculated reflectivity data, and the transformed other of the observed reflectivity data and the calculated reflectivity data on the at least one parameter further comprises:
    constructing a merit function for the transformed one of the observed reflectivity data and the calculated reflectivity data, and the transformed other of the observed reflectivity data and the calculated reflectivity data; and
    minimizing the merit function on the at least one parameter.

13. The method recited in claim 7 above, wherein finding agreement between the transformed one of the observed reflectivity data and the calculated reflectivity data, and the transformed other of the observed reflectivity data and the calculated reflectivity data on the at least one parameter further comprises:
    generating a plurality of instances of the transformed calculated reflectivity data, each of said plurality of instances of the transformed calculated reflectivity data being evaluated at unique parameter values for the at least one parameter;
    identifying one of the plurality of instances of the transformed calculated reflectivity data based on the transformed observed reflectivity data; and
    identifying a value for the at least one parameter associated with the identified instance of the transformed calculated reflectivity data.

14. The method recited in claim 13 above, wherein identifying one of the plurality of instances of the transformed calculated reflectivity data based on the transformed observed reflectivity data further comprises:
   comparing the transformed observed reflectivity to at least some of the plurality of instances of the transformed calculated reflectivity data; and
   resolving the value for the at least one parameter associated with the identified instance based on the comparison.

15. The method recited in claim 3 above, wherein the at least one parameter is associated with a respective at least one structure for the wafer, the method further comprises:
   controlling a process on the structure for the wafer based on the value for the at least one parameter.

16. The method recited in claim 3 above, wherein the calculated reflectivity data for the wafer comprises a simplified optical model as a function of exactly one parameter, said exactly one parameter representing an attribute of a portion of said wafer affecting reflective properties of said wafer in any calculable way.

17. The method recited in claim 16 above, wherein the attribute of the portion of said wafer is one of a refractive index, a film thickness, a trench depth, a trench depth in substrate, and a thickness of a multilayer dielectric stack.

18. The method recited in claim 15 above, wherein the calculated reflectivity data for the wafer comprises a simplified optical model as a function of at least two parameters, said at least two parameters representing at least two attributes of one or more portions of said wafer affecting reflective properties of said wafer in any calculable way.

19. The method recited in claim 18 above, wherein the at least two attributes of the one or more portion of said wafer are any combination of a refractive index, a film thickness, a trench depth, a trench depth in substrate, and a thickness of a multilay,er dielectric stack.

20. The method recited in claim 18 above, wherein the simplified optical model is a function of reflectivity being proportional to a sum of reflectivity from each region represented by the at least two parameters.

21. The method recited in claim 3 above, wherein receiving observed reflectivity data from a surface of a wafer further comprises:
   acquiring observed reflectivity data in-situ from a surface of a wafer.

22. The method recited in claim 3 above, wherein the at least one parameter is associated with a respective at least one structure for the wafer, the method further comprises:
   controlling a process on the structure for the wafer based on the value for the at least one parameter.

23. The method recited in claim 22 above further comprises:
   comparing the value for the at least one parameter with a stop value for the parameter at an end process state for the structure for the wafer.

24. The method recited in claim 3 above further comprises:
   receiving second observed reflectivity data from the surface of the wafer;
   obtaining calculated reflectivity data for the wafer, said calculated reflectivity data being a function of at least one parameter;
   transforming one of the second observed reflectivity data and the calculated reflectivity data;
   transforming the other of the second observed reflectivity data and the calculated reflectivity data to coincide with the transformed one of the observed reflectivity data and the calculated reflectivity data;
   finding agreement between the transformed one of the second observed reflectivity data and the calculated reflectivity data, and the transformed other of the second observed reflectivity data and the calculated reflectivity data on the at least one parameter; and
   determining a value for the at least one parameter based on the agreement.

25. The method recited in claim 24 above, wherein finding agreement between the transformed one of the second observed reflectivity data and the calculated reflectivity data, and the transformed other of the second observed reflectivity data and the calculated reflectivity data on the at least one parameter further comprises:
   determining a set of possible values for at least one parameter of the wafer;
   solving the calculated reflectivity data for the wafer for the set of possible values for at least one parameter; and
   saving a solution set of calculated reflectivity data and parameter value for the set of possible values for at least one parameter respective..

26. The method recited in claim 25 above, wherein determining a value for the at least one parameter based on the agreement further comprises:
   identifying one of the solution set of calculated reflectivity data based on the second observed reflectivity data; and
   identifying the parameter value associated with the selected one of the solution set of calculated reflectivity data.

27. The method recited in claim 20 above, wherein transforming one of the observed reflectivity data and the calculated reflectivity data further comprises:
   finding a vertical extent of the one of the observed reflectivity data and the calculated reflectivity data; and
   scaling the one of the observed reflectivity data and the calculated reflectivity data based on the vertical extent of the one of the observed reflectivity data and the calculated reflectivity data.

28. The method recited in claim 27 above further comprises:
   averaging the scaled one of the observed reflectivity data and the calculated reflectivity data.

29. The method recited in claim 28 above, wherein transforming the other of the observed reflectivity data and the calculated reflectivity data further comprises:
   finding a vertical extent of the other of the observed reflectivity data and the calculated reflectivity data; and
   scaling the other of the observed reflectivity data and the calculated reflectivity data based on the vertical extent of the other of the observed reflectivity data and the calculated reflectivity data.

30. The method recited in claim 29 above further comprises:
   averaging the scaled other of the observed reflectivity data and the calculated reflectivity data.

31. The method recited in claim 30 wherein the scaled one of the observed reflectivity data and the calculated reflectivity data coincides with the scaled other of the observed reflectivity data and the calculated reflectivity data.

32. The method recited in claim 31, wherein a vertical extent of the scaled one of the observed reflectivity data and the calculated reflectivity data has a value of one and a vertical extent of the other of the observed reflectivity data and the calculated reflectivity data also has a value of one.

33. The method recited in claim 30 above, wherein the averaged, scaled one of the observed reflectivity data and the calculated reflectivity data coincides with the averaged, scaled other of the observed reflectivity data and the calculated reflectivity data.

34. The method recited in claim 33 above, wherein an average of the averaged, scaled one of the observed reflectivity data and the calculated reflectivity data has an approximate value of zero and an average of the averaged, scaled other of the observed reflectivity data and the calculated reflectivity data also has an approximate value of zero.

35. The method recited in claim 30 above, wherein finding agreement between the transformed one of the observed reflectivity data and the calculated reflectivity data, and the transformed other of the observed reflectivity data and the calculated reflectivity data on the at least one parameter further comprises:

constructing a merit function for the transformed one of the observed reflectivity data and the calculated reflectivity data, and the transformed other of the observed reflectivity data and the calculated reflectivity data; and a minimizing the merit function on the at least two parameters.

36. The method recited in claim 35 above, wherein finding agreement between the transformed one of the observed reflectivity data and the calculated reflectivity data, and the transformed other of the observed reflectivity data and the calculated reflectivity data on the at least one parameter further comprises:

generating a plurality of instances of the transformed calculated reflectivity data, each of said plurality of instances of the transformed calculated reflectivity data being evaluated at a unique parameter value for each of the at least two parameters;

identifying one of the plurality of instances of the transformed calculated reflectivity data based on the transformed observed reflectivity data; and identifying a value for each of the at least two parameters associated with the identified instance of the transformed calculated reflectivity data.

37. The method recited in claim 20 above, wherein the observed reflectivity data is a ratio of spectral reflectivity of the surface of the wafer and a reference reflectivity spectrum.

38. The method recited in claim 15 above, wherein receiving observed reflectivity data from a surface of a wafer further comprises:

acquiring observed reflectivity data in-situ from a surface of a wafer.

39. The method recited in claim 7 above, wherein observed reflectivity data and the calculated reflectivity data comprise plurality of wavelengths.

40. The method recited in claim 23 above, wherein observed reflectivity data and the calculated reflectivity data comprise plurality of wavelengths.

41. The method recited in claim 26 above, wherein observed reflectivity data and the calculated reflectivity data comprise plurality of wavelengths.

42. The method recited in claim 30 above, wherein observed reflectivity data and the calculated reflectivity data comprise plurality of wavelengths.

* * * * *